(12) United States Patent
Savran et al.

(10) Patent No.: US 8,933,384 B2
(45) Date of Patent: Jan. 13, 2015

(54) MULTI-TECHNIQUE IMAGING SYSTEM USING VERTICAL MOTION OF STAGE TO SWITCH IMAGING TECHNIQUES

(75) Inventors: Cagri A. Savran, West Lafayette, IN (US); Khalid M. Arif, Lahore (PK)

(73) Assignee: Purdue Research Foundation, West Lafayette, IN (US)

( * ) Notice: Subject to any disclaimer, the term of this patent is extended or adjusted under 35 U.S.C. 154(b) by 239 days.

(21) Appl. No.: 13/430,316

(22) Filed: Mar. 26, 2012

(65) Prior Publication Data

US 2012/0241596 A1   Sep. 27, 2012

Related U.S. Application Data

(60) Provisional application No. 61/467,815, filed on Mar. 25, 2011.

(51) Int. Cl.
| | |
|---|---|
| G02B 27/00 | (2006.01) |
| G02B 7/00 | (2006.01) |
| H01L 27/00 | (2006.01) |
| G01N 21/55 | (2014.01) |
| G02B 21/00 | (2006.01) |
| G02B 21/18 | (2006.01) |
| G02B 21/36 | (2006.01) |
| G01N 21/47 | (2006.01) |
| G01N 21/64 | (2006.01) |
| G01N 21/65 | (2006.01) |

(52) U.S. Cl.
CPC ............ *G01N 21/55* (2013.01); *G02B 21/0008* (2013.01); *G02B 21/18* (2013.01); *G02B 21/36* (2013.01); *G01N 21/4788* (2013.01); *G01N 21/553* (2013.01); *G01N 21/554* (2013.01); *G01N 21/6456* (2013.01); *G01N 21/65* (2013.01); *G01N 2021/479* (2013.01); *G01N 2021/558* (2013.01); *G01N 2201/0221* (2013.01); *G01N 2201/0693* (2013.01)
USPC ..................... 250/208.1; 250/201.3

(58) Field of Classification Search
CPC ............ G02B 7/36; G02B 7/28; G02B 7/346; G02B 7/32; G01J 1/04; G01J 2001/0257; G01J 2021/015; G01J 2021/0175; B65H 2553/414; B65H 2553/46
USPC .......... 250/21, 208.1, 201.2, 559.4, 306, 307; 250/216; 359/369, 372, 388, 393, 368; 356/399–402
See application file for complete search history.

(56) References Cited

U.S. PATENT DOCUMENTS 6,635,011 B1 * 10/2003 Ozawa et al. ................. 600/178
2007/0120069 A1 * 5/2007 Takamizawa .............. 250/458.1

* cited by examiner

*Primary Examiner* — Georgia Y Epps
*Assistant Examiner* — Carolynn A Moore
(74) *Attorney, Agent, or Firm* — Purdue Research Foundation

(57) ABSTRACT

A system for and method of performing multi-technique imaging. Such multi-technique imaging system includes a surface for supporting a specimen and at least two illumination sources for producing light radiation. The system also includes a plurality of reflective and refractive devices arranged to direct at least part of the light radiation from each of the at least two illumination sources to the surface such that at least part of the light radiation from each of the at least two illumination sources illuminates substantially the same area on the surface. The system also includes a sensor configured to receive light radiation from the at least two illumination sources reflected by the specimen and/or that pass by the specimen. The system also includes a power source configured to power the at least two illumination sources and the sensor.

20 Claims, 16 Drawing Sheets

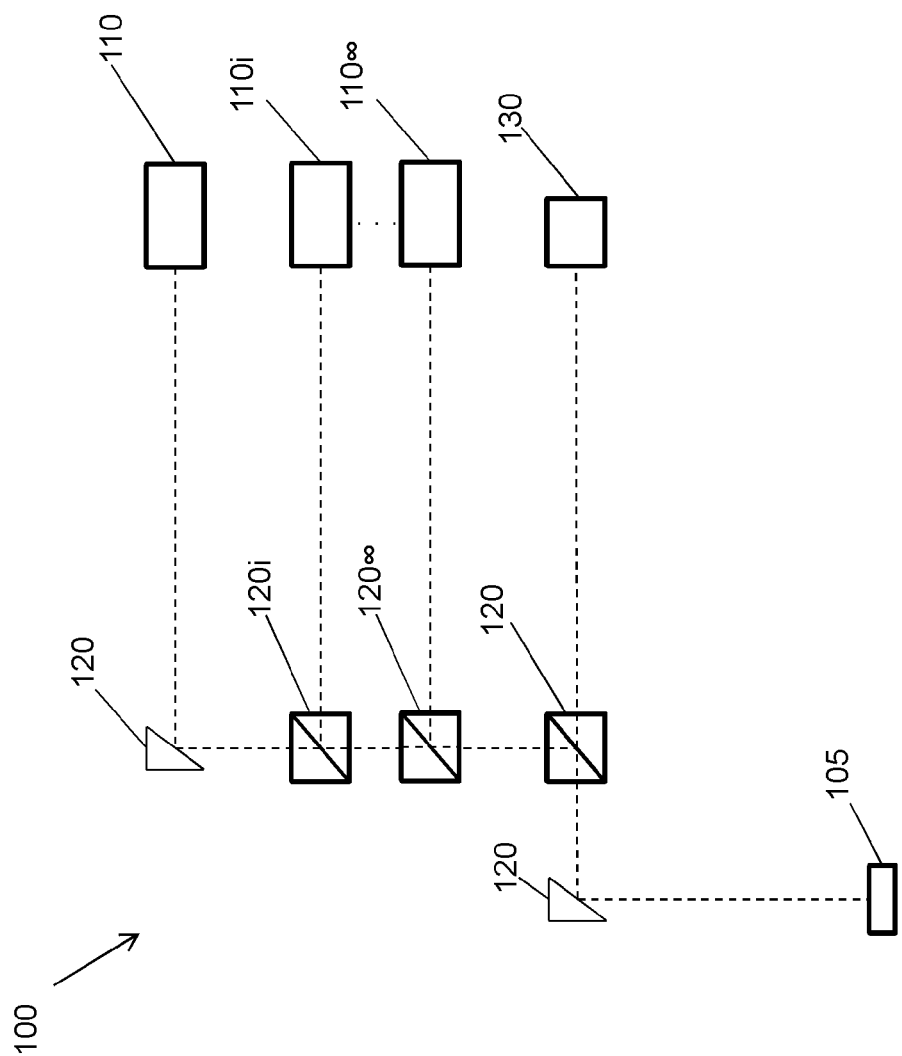

MULTI-TECHNIQUE IMAGING SYSTEM USING VERTICAL MOTION OF STAGE TO SWITCH IMAGING TECHNIQUES

CROSS REFERENCE TO RELATED APPLICATIONS

This patent application claims the benefit of and incorporates by reference herein the disclosure of U.S. Ser. No. 61/467,815, filed Mar. 25, 2011.

U.S. GOVERNMENT SUPPORT

This invention was made with government support under 5R21EB008154 awarded by the National Institute of Health. The government has certain rights in the invention.

BACKGROUND

Imaging and diffraction-based measurements are widely-used in nearly all areas of research. However, most current imaging systems are designed for specific table-top experiments, occupy large spaces, and require trained personnel for operation. Furthermore, most imaging systems today are designed to handle only one technique of microscopy, e.g., bright field imaging. In order to perform more than one optical analysis technique (i.e., illumination and measurement by multiple sources, such as, for example, white light illumination for bright field imaging and laser illumination for diffractometry), a user today must typically transport the user's sample from one imaging system to another imaging system. Unfortunately, each time a sample is positioned under a different imaging system, the sample must be re-positioned and re-aligned. Such positioning can be cumbersome and lead to inaccuracies. Finally, imaging equipment in use today is typically large and not portable.

A compact, portable system that can perform multi-technique imaging including bright field imaging and diffractometric analysis of sample chip surfaces can be extremely useful both in lab usage and point-of-care applications. Therefore, there exists a need for a system for performing optical imaging and diffraction measurements, analyze the associated data, store the raw data and the analyzed data, and display and communicate the analyzed data, all in one package that contains light-weight components and occupies a relatively small space, without the need of transporting the analyzed specimen from one experimental setup to another.

SUMMARY

The present disclosure discloses a system and method for performing multi-technique imaging. In one embodiment, such a system includes a surface for supporting a specimen and at least two illumination sources for producing light radiation. The system also includes a plurality of reflective and refractive devices configured to direct at least part of the light radiation from each of the at least two illumination sources to the surface such that at least part of the light radiation from each of the at least two illumination sources illuminate substantially the same area on the surface (i.e. illuminating the same area on the specimen). The system further includes a sensor configured to receive light radiation from the at least two illumination sources reflected by the specimen and/or that pass by the specimen. The system additionally includes a power source configured to power the at least two illumination sources and the sensor.

In one embodiment, a method for performing multi-technique imaging includes the step of arranging a plurality of reflective and/or refractive devices to direct at least part of light radiation from each of at least two illumination sources in the direction of a surface supporting a specimen such that at least part of the light radiation from each of the at least two illumination sources illuminate substantially the same area on the surface and pass through a shared reflective and/or refractive device. The method also includes the step of activating the at least two illumination sources to produce light radiation. The method further includes collecting the light radiation from the at least two illumination sources reflected by the specimen.

BRIEF DESCRIPTION OF DRAWINGS

The features and advantages of this disclosure, and the manner of attaining them, will be more apparent and better understood by reference to the accompanying drawings, wherein:

FIG. 1 depicts a schematic view of one embodiment of the system for performing multi-technique imaging according to the present disclosure.

DETAILED DESCRIPTION

Figure 2A:
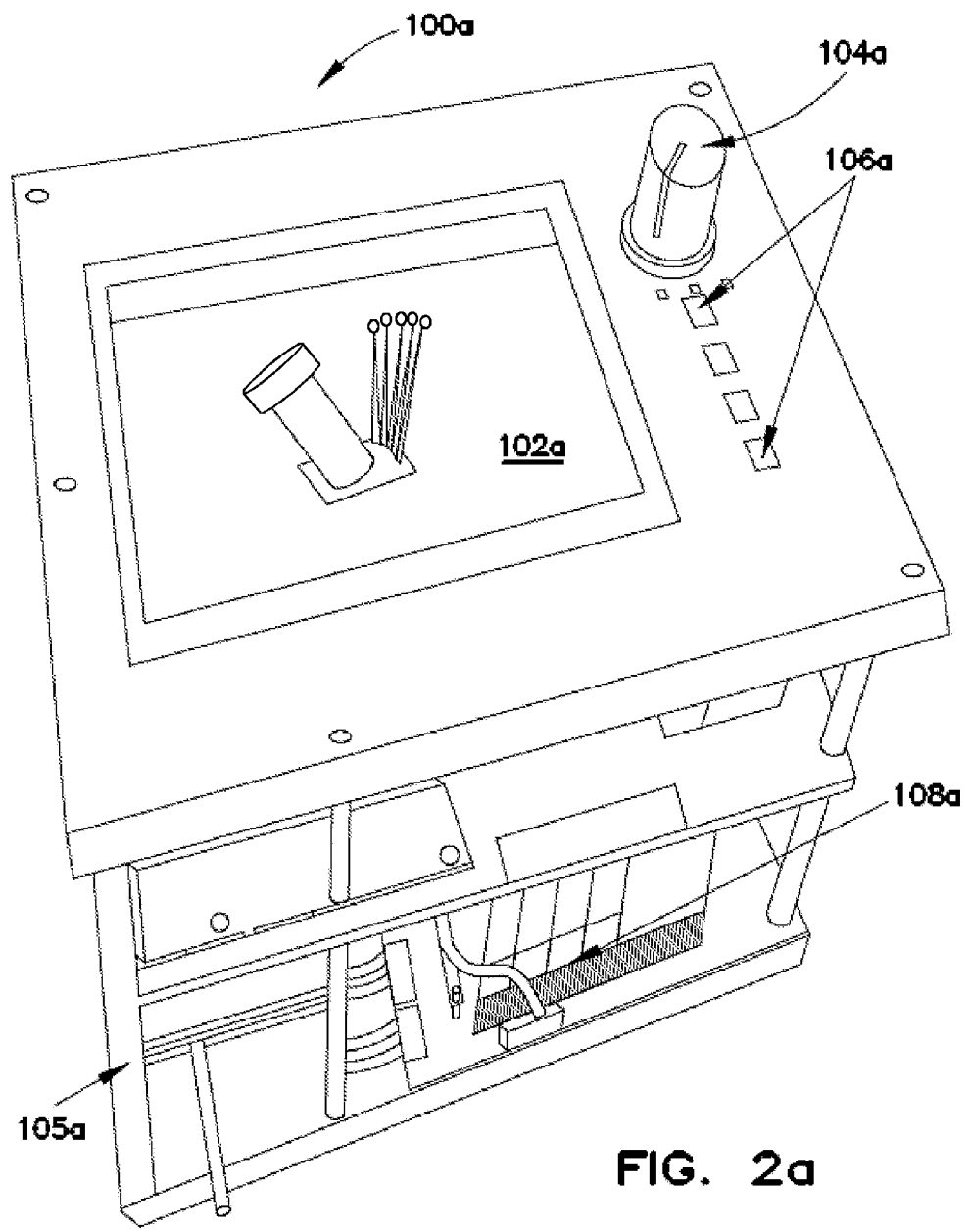
FIG. 2a depicts a perspective view of one embodiment of a portable multi-technique imaging system (PMMIS) including a screen for displaying data, according to the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one of ordinary skill in the art to which this disclosure pertains.

A system of and method for performing multi-technique microscopic imaging is described in the present disclosure. FIG. 1 shows a diagram of an exemplary system 100 of at least one embodiment of the present disclosure. As shown in FIG. 1, the system 100 includes a stage 105 for supporting and manipulating a specimen, two or more illumination sources 110, and two or more reflective and/or refractive devices 120 that are arranged to direct at least part of the light radiation from the two or more illumination sources 110 to the stage 105, As described below, the illumination. sources 110 may be various devices that produce radiation including, light, such as, for example, a device for producing :laser light, a device for producing white light, and a device for producing colored light (i.e., non-white). It should be appreciated that the system according to the present disclosure is configured to utilize various sources of light. No limitation is intended based on the use of the term light. A light can be configured to provide light in any part of the electromagnetic spectrum, including but not limited to visible light of different colors, including white light, infrared, X-ray, and other type of light known to a person having ordinary skill in the art. Light can be of a highly propagating nature or of a collimated nature, e.g., a laser. It should be noted that there may be a number of reflective and/or refractive optical devices or a combination of optical devices such as an objective, lens to direct light and collect light from the stage. As shown in FIG. 1, there may be any number of illumination sources 110 and reflective devices 120. The dashed lines in FIG. 1 (as well as in other figures of various embodiments of system 100 show pathways of light radiation from the illumination sources 110. The system 100 also includes a sensor 130 for receiving light radiation from the at least two illumination sources 110. It should be noted that the sensor 130 may receive light radiation that is reflected by the specimen and/or when the light radiation passes by the specimen. For example, the system 100 may be arranged such that the sensor is on the same side of the stage as the specimen (thereby receiving the reflected light radiation from the specimen) or such that the sensor is on the opposite side of the stage as the specimen (thereby receiving the light radiation after it passes by the specimen), While FIG. 1 only shows one sensor 130, the system 100 may include multiple sensors 130 for collecting light radiation. While not shown in FIG. 1 the system 100 also includes a power source for powering the illumination devices 110 and sensor 130. As described below, the arrangement of the system 100 allows a user to perform multiple imaging analysis techniques on a specimen without having to transport the specimen to and realign the specimen on multiple types of imaging equipment.

FIGS. 2a-2d, 3, and 4 show an example of the system 100, namely a portable multi-technique imaging system (PMMIS) 100a suitable for point of care applications. It should be appreciated that the system according the present disclosure is portable. Portability is intended to mean that the system of the present disclosure is transportable from one location to another location with ease and without the need for any special equipment or arrangement. For example, the system of the present disclosure may be placed on a lab bench, or easily carried by a person to another location where without limitation the system of the present disclosure is powered up by an internal power interface, e.g., a battery, the specimen is inserted into the system, the specimen is analyzed, the analyzed data is saved on to a memory device, e.g., a hard drive, and the analyzed data is communicated to another device using a wireless communication interface and over a network, e.g., the internet. FIG. 2a shows a perspective view of the PMMIS 100a. The PMMIS 100a depicted in FIG. 2a is a lightweight compact and portable microscopic imaging system that can operate both with AC or battery power, suitable for viewing microscopic details of a variety of specimens, such as, for example, geometries of a specimen on a test chip in the micrometer range. As discussed further below, the PMMIS 100a can be used with test chips with receptor sites and functionalized magnetic beads, which trap and localize molecular structures that are sized in the micrometer to nanometer range.

The PMMIS 100a depicted in FIG. 2a includes a screen or display 102a, a control knob 104a, control buttons 106a, manipulation stage 105a, communication and control circuits 108a, which includes an on-board computer, that connect and process information between the display 102a, control knob 104a, control buttons 106a, manipulation stage 105n, sensor 130a (not shown) to each other and other parts of the PMMIS 100a. The screen 102a is configured to display information and analysis results to the user regarding the light radiation received by the sensor 130a(discussed below). The screen 102a may be various types of devices known in the art designed to display electronic information. For example, the screen 102a may be a touch screen configured to present menus and read inputs from a user touching the screen 102a. The control knob 104a and the control buttons 106n may be configured to control various operations of the PMMIS 100a, including light intensity, activation of light sources, and powering the system on and off. While not shown in FIG. 2a, the PMMIS 100a may include wireless and/or wired communication provisions for communicating with external sources (e.g., a personal computer, an external display unit, a distant receiver and a printer).

Figure 2B:
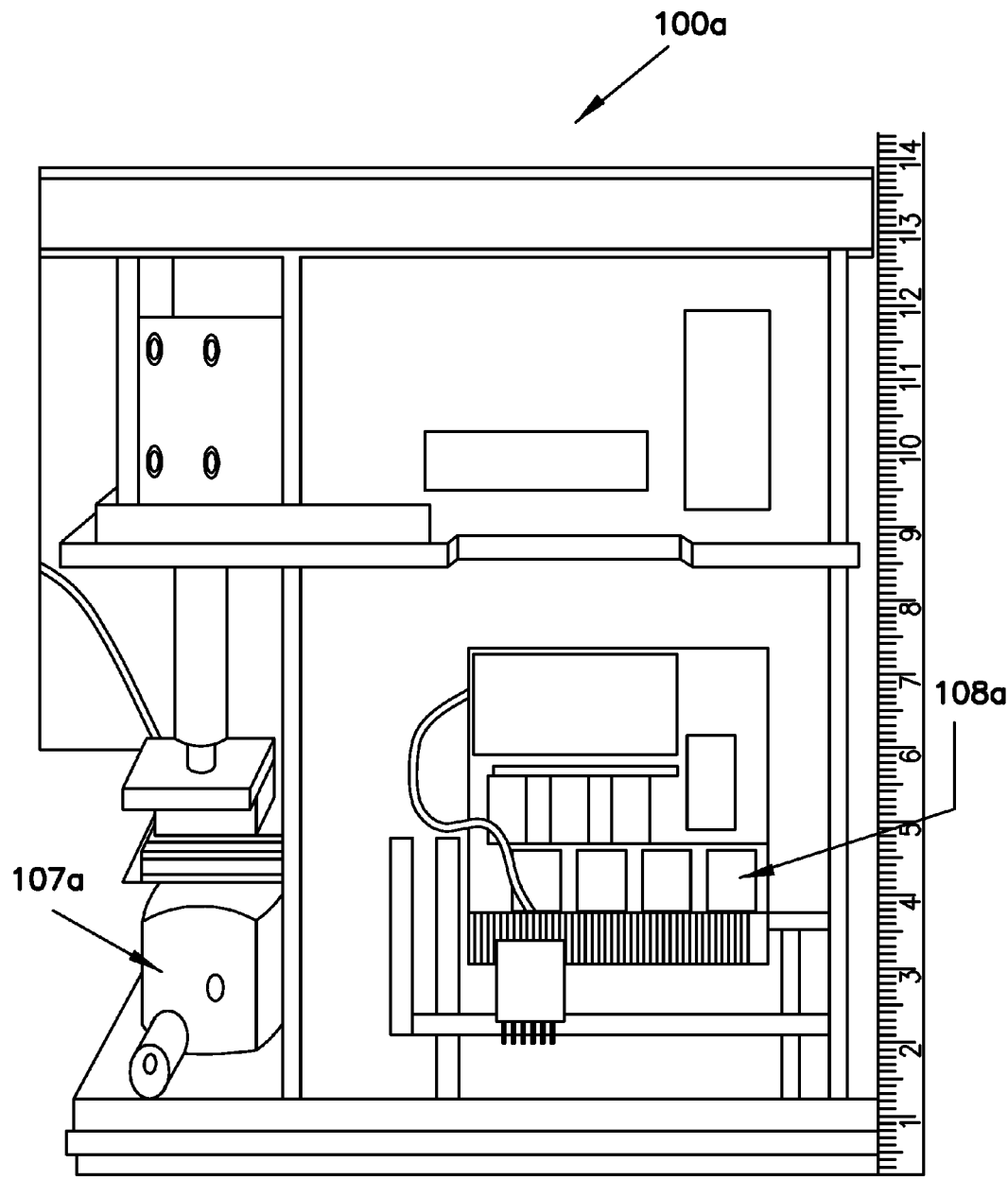
FIG. 2b depicts a side view of one embodiment of a PMMIS, showing the optical, electronic and manipulation stage components according to the present disclosure.
Figure 2C:
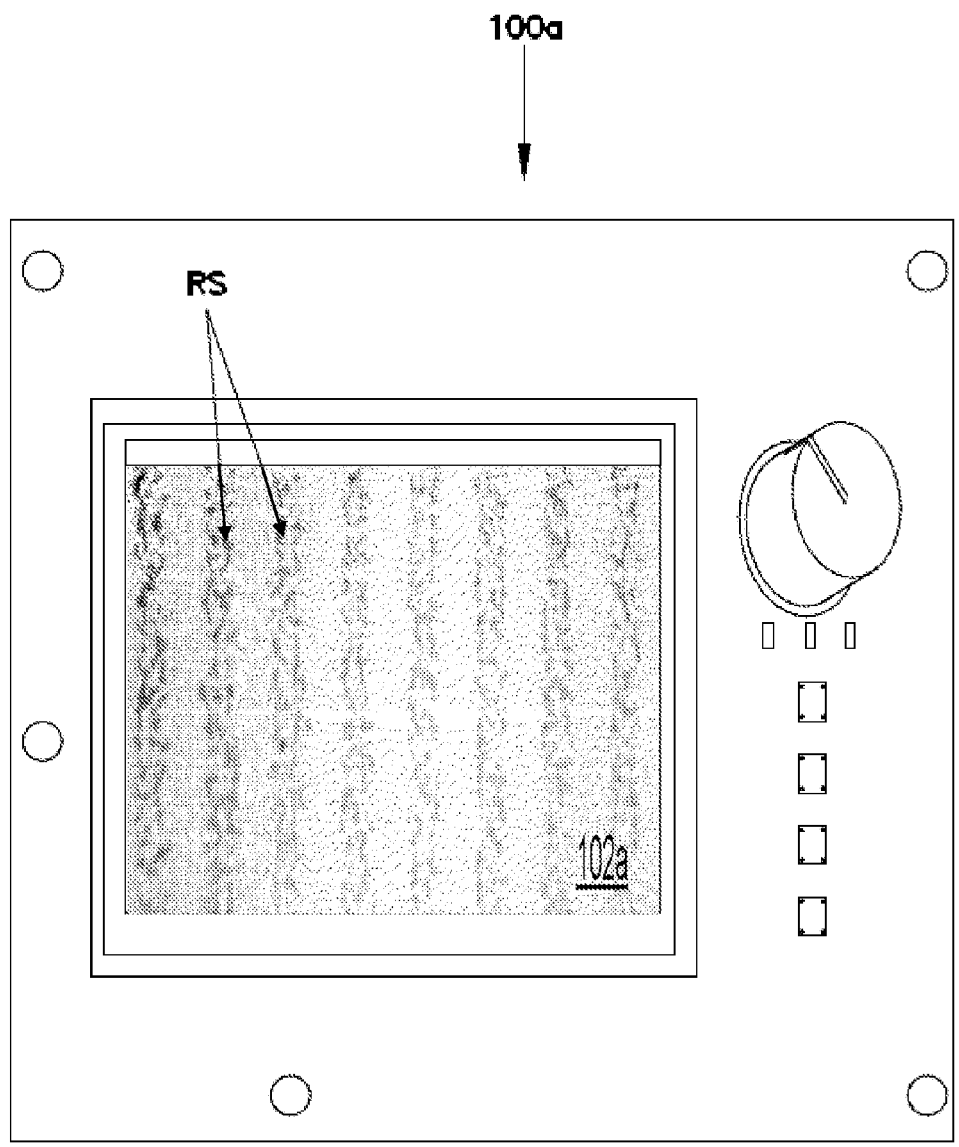
FIG. 2c depicts a top view of one embodiment of a PMMIS, showing the microscopic image of a specimen with receptor sites on the screen, according to the present disclosure.

Referring to FIGS. 2b and 2c, the PMMIS 100a of FIG. 2a is depicted from side and top view perspectives. Depicted in FIG. 2b, is a manipulator 107a that is configured to adjust the position of a specimen. The manipulator 107a may be any type of device configured to adjust the position of the specimen, such as, for example, a micro-manipulator. The manipulator 107a can be manually controlled or controlled electronically by use of servo and stepper motors, known to a person of ordinary skill in the art. For example, the vertical motion of the stage of the manipulator 107a may be controlled manually by a micrometer. The x and y (horizontal) motions of the stage may be controlled by two separate stepper motors with leadscrew interfaces. As noted previously, the motors may be controlled by the on-board computer. In one embodiment, a user can touch a button or portion of the screen and the stage will move right or left. Alternatively, a user can program the on-board computer to move the stage in a pre-determined state (e.g., to scan at least a part of the surface).

Shown in FIG. 2b is a manipulator 107a that is integrated in the PMMIS 100a. The communication and control circuits 108a may be configured to automatically control the manipulator 107a under control of software. FIGS. 2e-2f show an illustration of one embodiment of a manipulator 107a according to the present disclosure. In FIG. 2e, the manipulator 107a includes a first plate FP for supporting a specimen and a second plate SP for supporting the first plate FP and a first linear pack FLP that allows the first plate FP to slide relative to the second plate in the X direction as defined in FIG. 2e. In FIG. 2e, the manipulator 107a also includes a third plate TP for supporting the second plate SP and one or more second linear packs SLP that allow the second plate SP to slide relative to the third plate TP in the Y direction as defined in FIG. 2e. FIG. 2g shows an example of a first linear pack FLP and second linear pack SLP. The manipulator 107a also includes a shaft S that is integrated with the third plate TP such that all of the plates FP, SP, TP can be moved in the Z direction (as defined in FIG. 2e) manually or automatically through the use of various devices, such as, for example, a micrometer. FIGS. 2e and 2f also show calibration devices CD that allow the various plates FP, SP, TP to be moved along the X, Y, and Z directions. For each linear pack FLP, SLP, manipulator 107a may also include a corresponding stepper motor with lead screw calibration device that allows either a computer or user to electrically manipulate the position of the specimen in any of the X or Y directions as needed.

Shown in FIG. 2c is the top view of PMMIS 100a showing a real-time microscopic image of a specimen that has microscopic receptor sites (RS) with magnetic micro and nanoparticles immobilized in a manner mediated by a biomolecular reaction. The on-board computer of PMMIS 100a can be programmed to perform multiple types of image analysis including but not limited to identifying and counting entities and analyzing their properties.

Figure 2D:
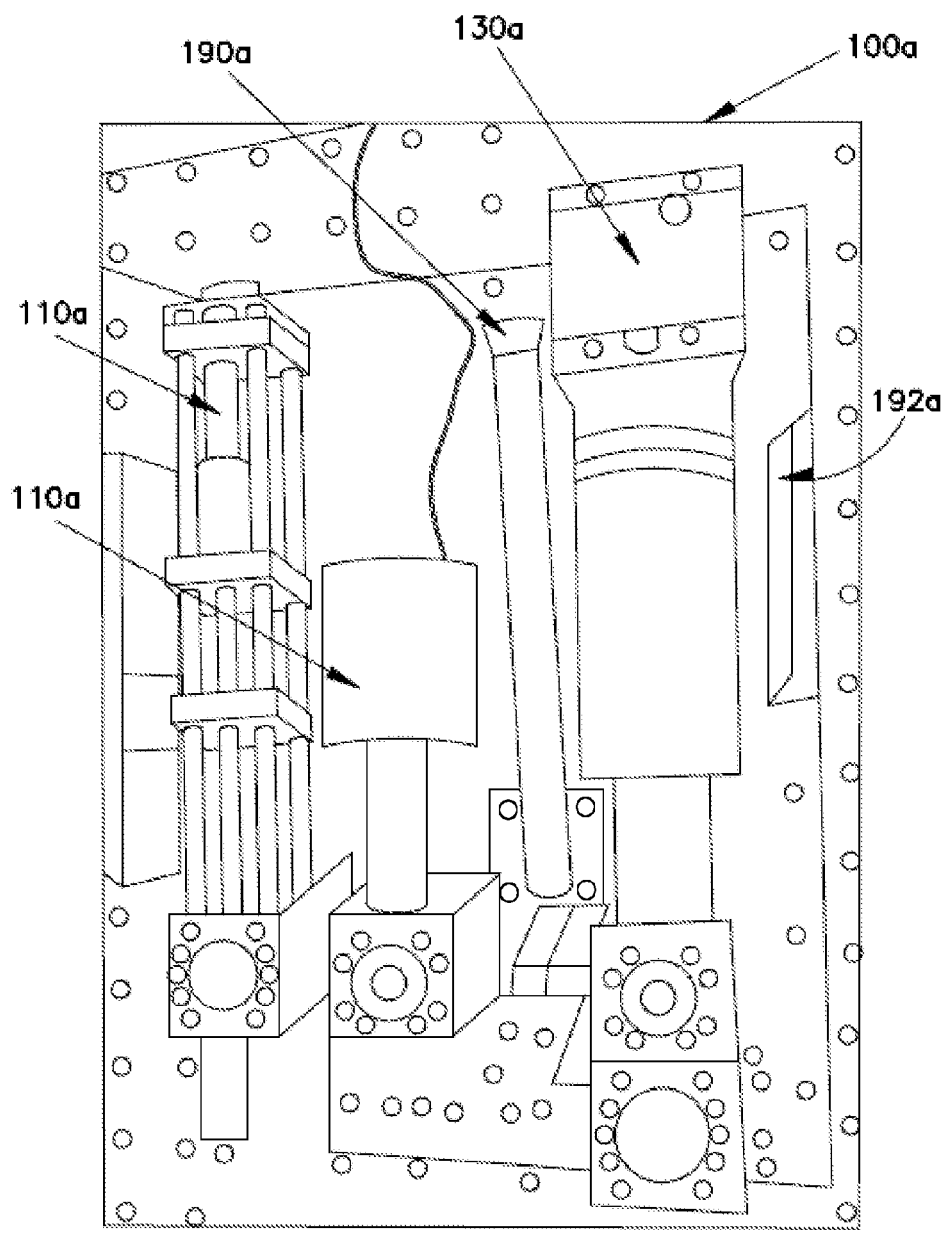
FIG. 2d depicts a top view of one embodiment of a PMMIS, revealing the internal optical components, according to the present disclosure.
Figure 2E:
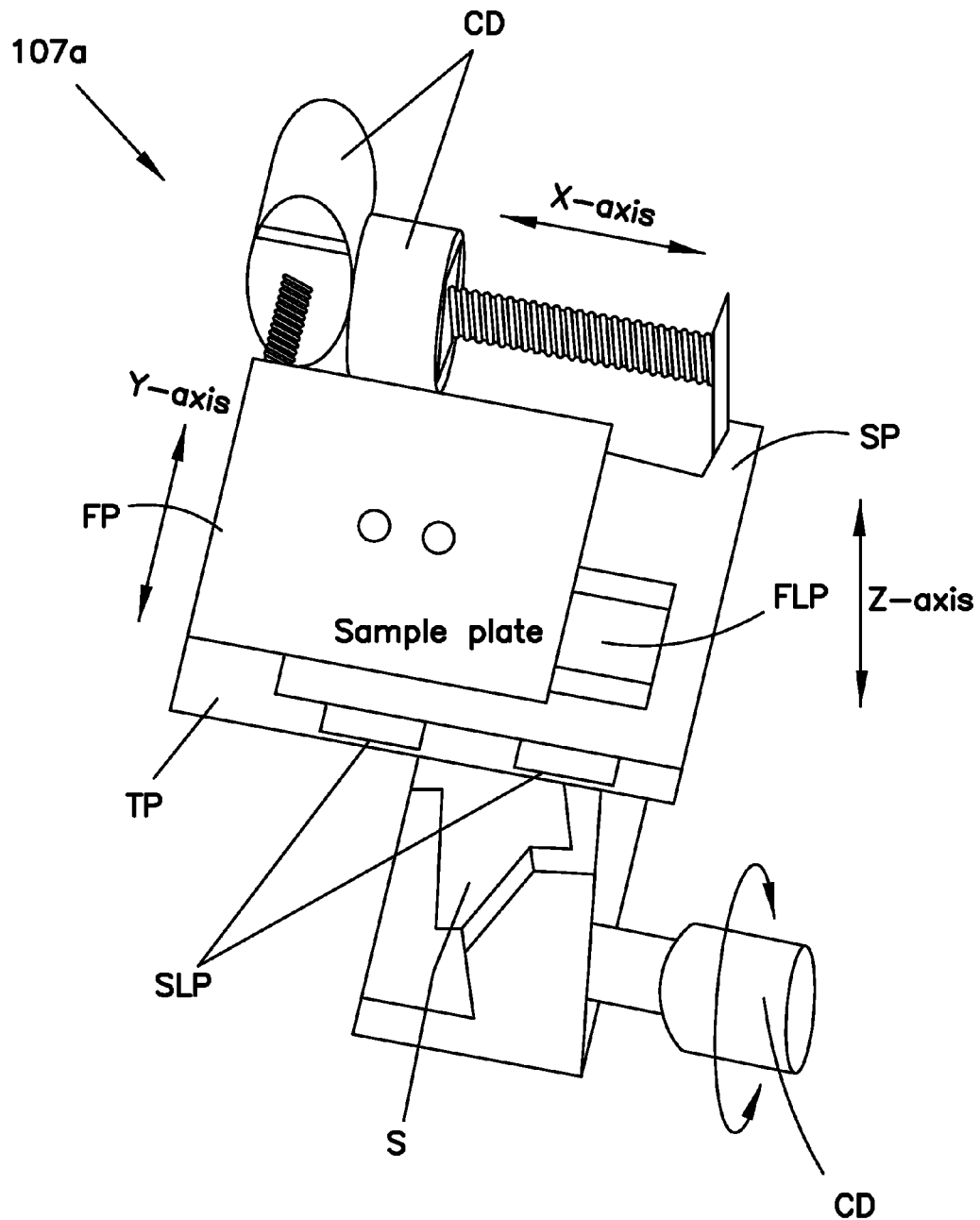
FIGS. 2e-2g depict an illustration of one embodiment of a manipulator according to the present disclosure.
Figure 2G:
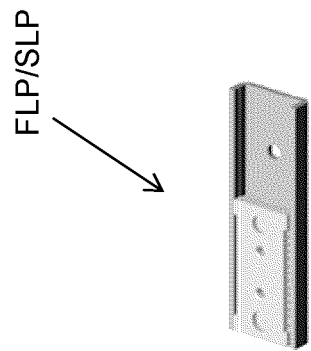
Figure 2F:
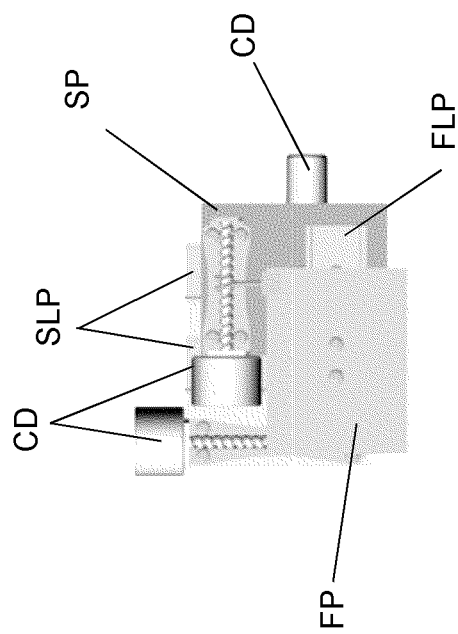
Figure 3:
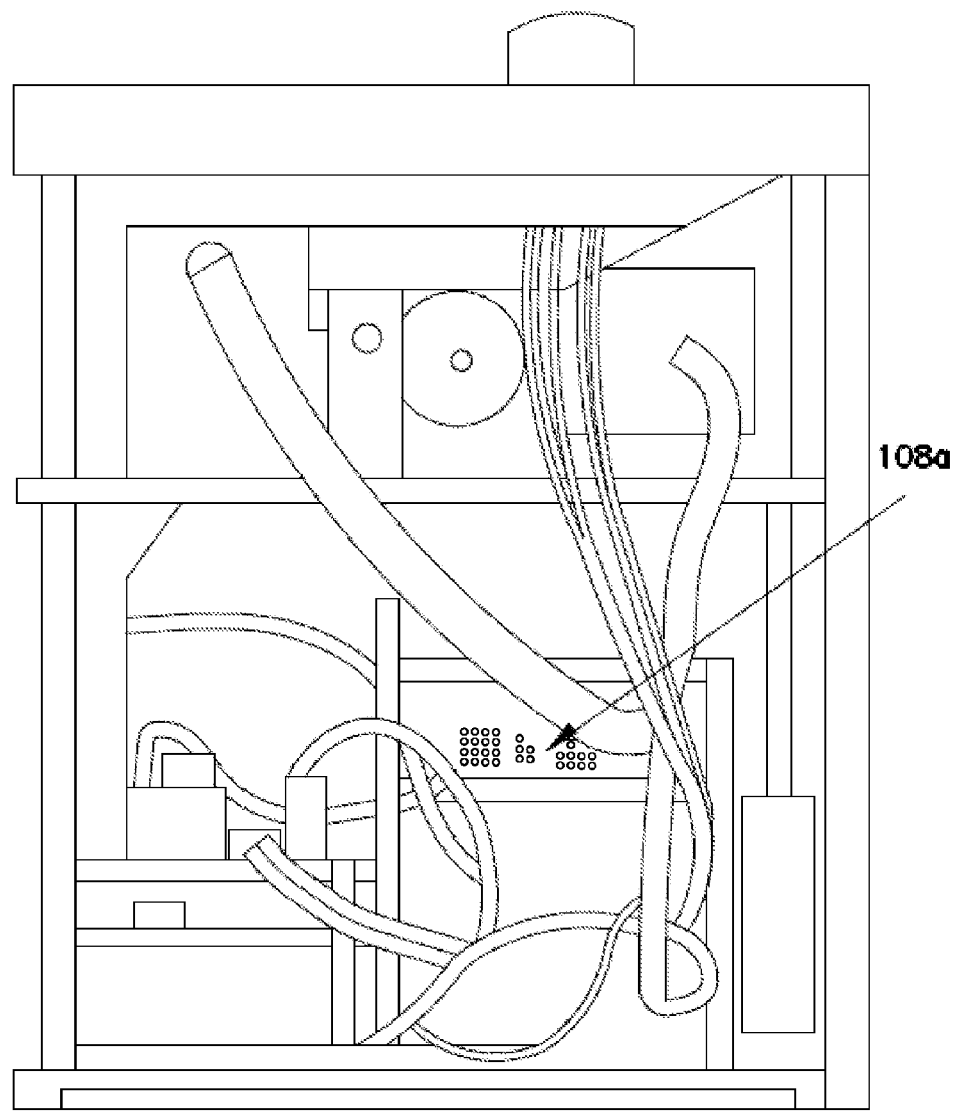
FIG. 3 depicts a view of a side of a PMMIS, revealing electronic circuits for analysis, control, and communication according to one embodiment of the present disclosure.

Referring to FIG. 2d, the PMMIS of FIG. 2a is depicted with the screen lifted to reveal internal components of the PMMIS. FIG. 2d shows two illumination sources 110a (namely, a bright field (white light) source and a laser source), a sensor (namely, a charge coupled device (CCD)) 130a, a wireless antenna 190a, and a motion controller 192a (shown in FIG. 2b) for the manipulator 107a. The sensor can be various devices for collecting light radiation, such as, for example, the CCD model DCU223C from Thorlabs. Alternatively, the sensor may be various other CMOS devices or digital imaging sensors instead of a CCD. For example, the sensor may be a photodiode digital image sensor. The motion controller 192a may be part of the communication and control circuits 108a, more clearly depicted in FIGS. 2b and 3.

While the PMMIS 100a depicted in FIGS. 2a-d and 3 includes bright field and laser diffractometry capabilities, the PMMIS 100a may have additional or alternative capabilities by way of other microscopic techniques. Such other techniques as well as bright field and diffractometry techniques are discussed below.

Figure 4A:
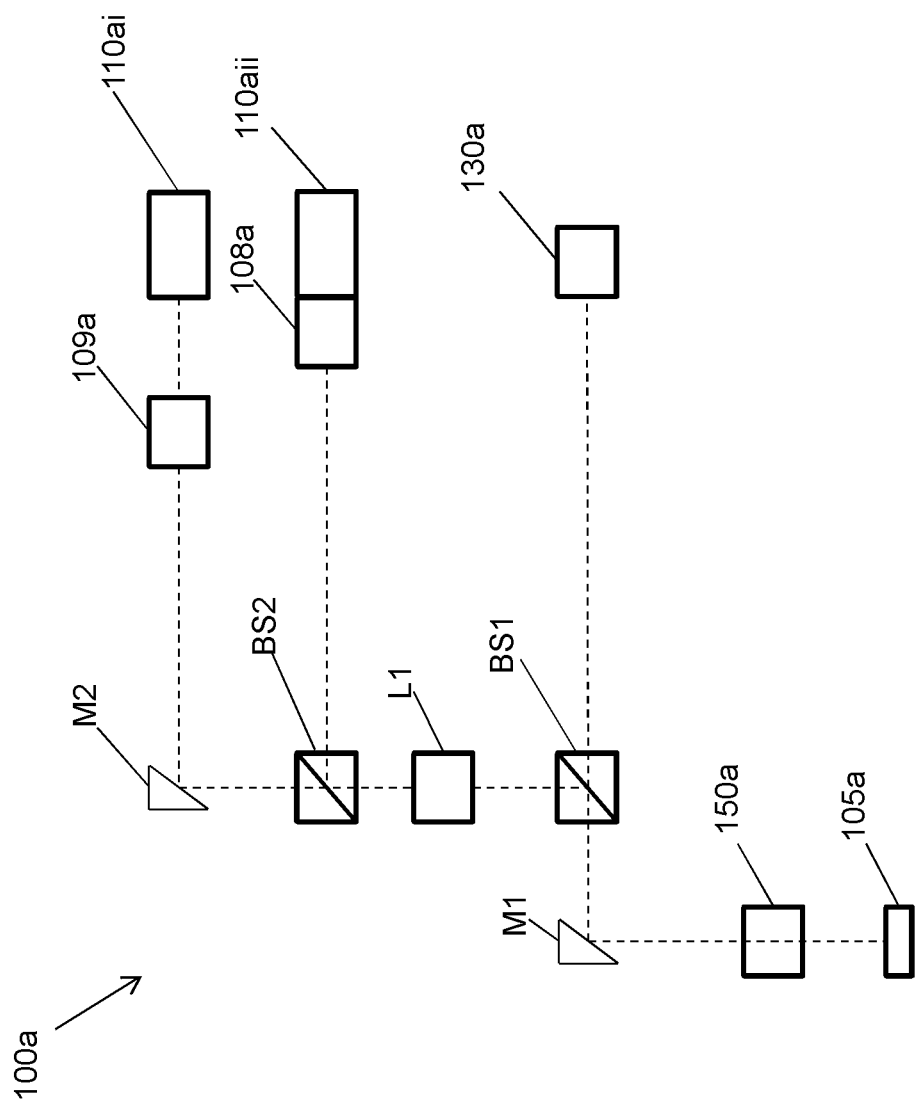
FIG. 4a depicts a schematic view of an exemplary embodiment of a PMMIS according to the present disclosure with bright field and laser illumination of a target chip.

Referring to FIG. 4a, a schematic of the PMMIS 100a of FIGS. 2a-2d and 3 is depicted. As shown in FIG. 4a, a laser diode 110ai (e.g., a 635 nm laser source) is used to generate laser light. The laser light from the laser diode 110ai is polarized as it passes through a polarizer 109a and reflected (and redirected) by striking a reflection surface M2. As shown in FIG. 4a, the laser light passes through reflective device BS2 and lens L1 and is redirected by reflective device BS1. The laser light is then reflected off of reflective device M1 and passes through objective lens 150a where it strikes the stage 105a for supporting a specimen. Also shown in FIG. 4a, a white light 110aii (e.g., a 3500K light source, bright field source) is used to generate a bright field (e.g. white) light. It should be noted that the white light may be a single LED combined with a color wheel or a collection of LEDs with different colors to generate illumination with different wavelengths. This arrangement can be used for white light imaging, diffractometry, multi-wavelength bright field imaging as well as fluorescence microscopy, by introducing a movable wavelength filter before the image sensor 130a.

Figure 4B:
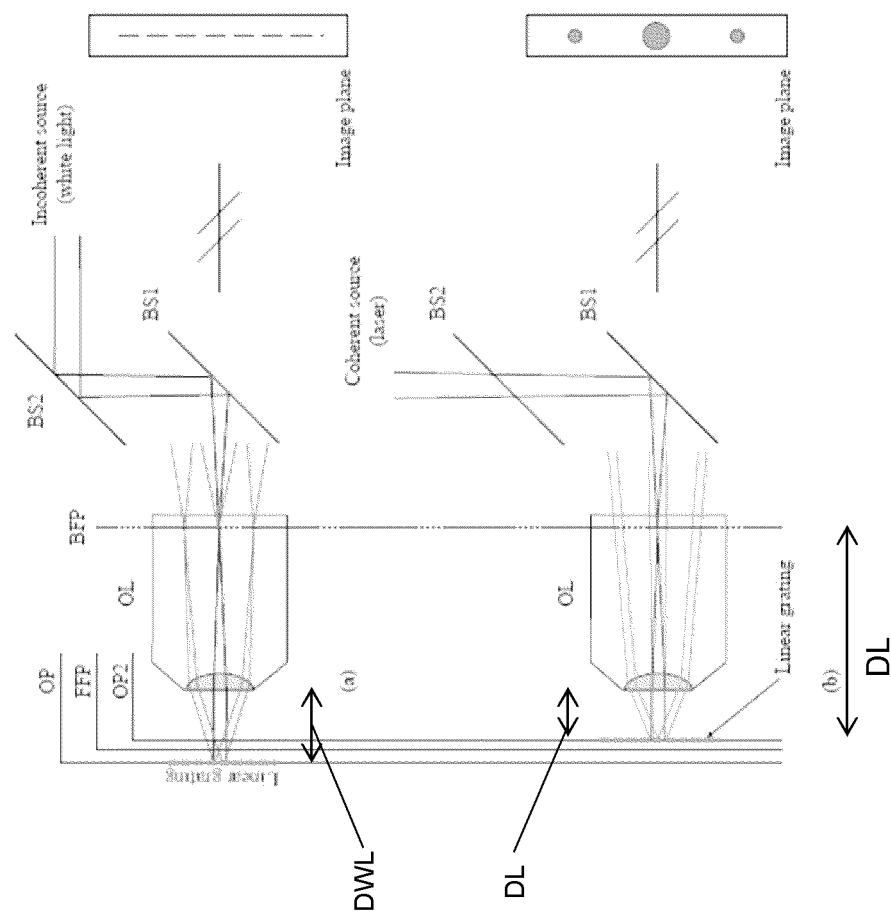
FIG. 4b depicts a schematic of an exemplary embodiment of a PMMIS according to the present disclosure showing bright field imaging and diffractometry performed on the same stage, using the same objective lens, and the same image plane of the PMMIS and resulting images on the image plane.

In FIG. 4a, the bright field light is condensed through a condenser 108a and is redirected by reflective device BS2. The bright field light then passes through lens L1 and is redirected by reflective device BS1. The bright field light then is redirected by reflective device M1 so that it passes through objective lens 150a and strikes the stage 105a. Using the laser diode 110ai and white light 110aii, the PMMIS 100a is able to provide epi-illumination for bright field imaging and diffraction measurement of specimens. The reflection/diffraction from the specimen passes through the objective lens 150a and is captured by the image sensor (e,g. a CCD) 130a, The reflective and refractive devices 120 of a system 100 of the present disclosure may be any type of device configured to reflect or refract light radiation known to one skilled in the art, such as, for example, a mirror or a refractive component such as a lens. The reflective and refractive devices can include, but are not limited to, mirrors, dichroic mirrors, and converging and diverging lenses. The reflective and refractive devices may be selected and positioned for particular results. For example, the reflective and refractive devices may be arranged such that the incident light is focused at the back focal plane of an objective lens, so as to generate a plane wave front to impinge on the specimen that is the subject of a diffraction measurement. When the specimen is closer to the objective lens than the lens' front focal plane, the diffraction pattern generated by the specimen (e.g. a linear grating) diverges and is directed into the image sensor without any significant interference of the diffraction pattern components (or modes). The specimen can be moved further away (beyond the front focal plane or FFP of the objective lens) for bright field imaging. FIG. 4b shows an example of the specimen being moved closer to the objective lens (OL) for diffractometry and away from it for bright field imaging. In particular, in FIG. 4b, the distance DWL between the specimen and the closest part of the objective lens for bright field imaging is greater than the distance DL between the specimen and the closest edge of the objective lens for diffractometry. Such a scheme would also allow "co-incident" imaging and diffractometry of the same area on the specimen using a single objective lens and a single image sensor (such as a CCD).

Figure 7:
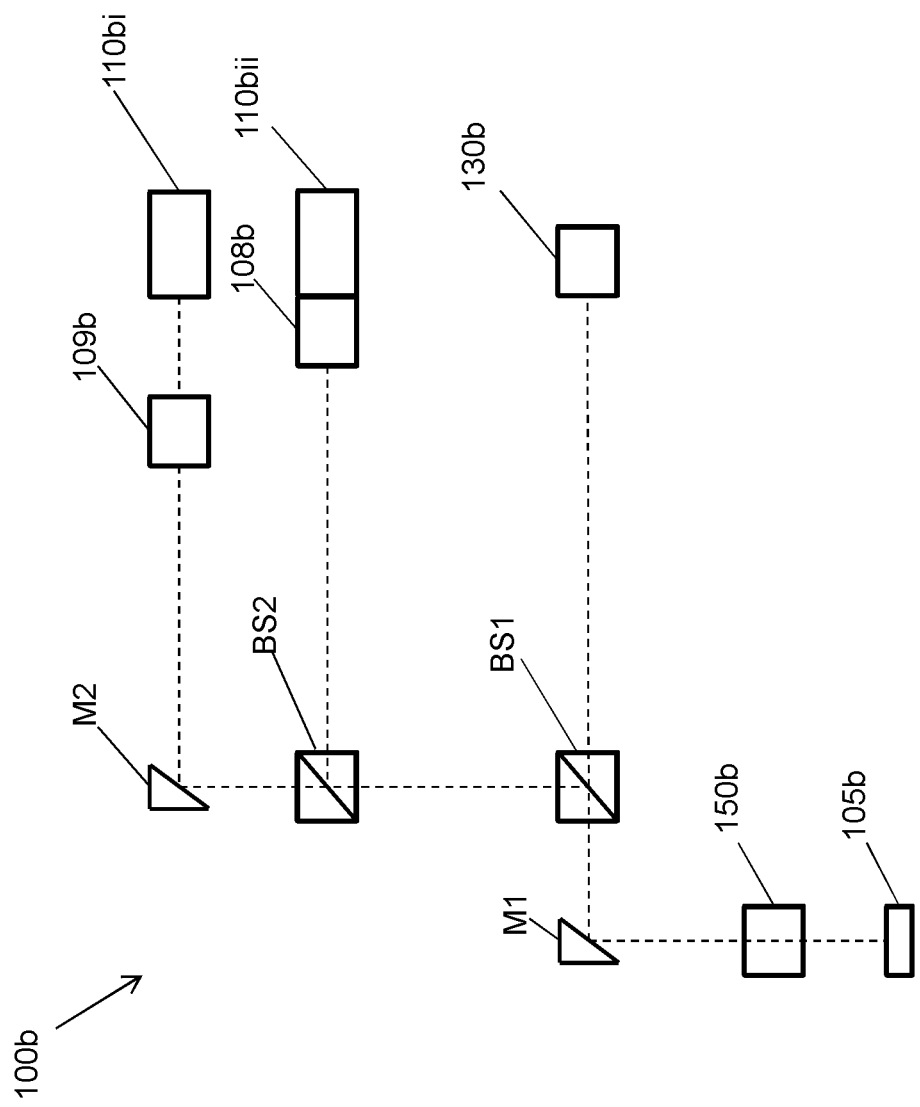
FIG. 7 depicts a schematic view of an exemplary system according to at least one embodiment of the present disclosure utilizing a bright field apparatus and a laser speckle apparatus for illumination of a target chip.
Figure 8:
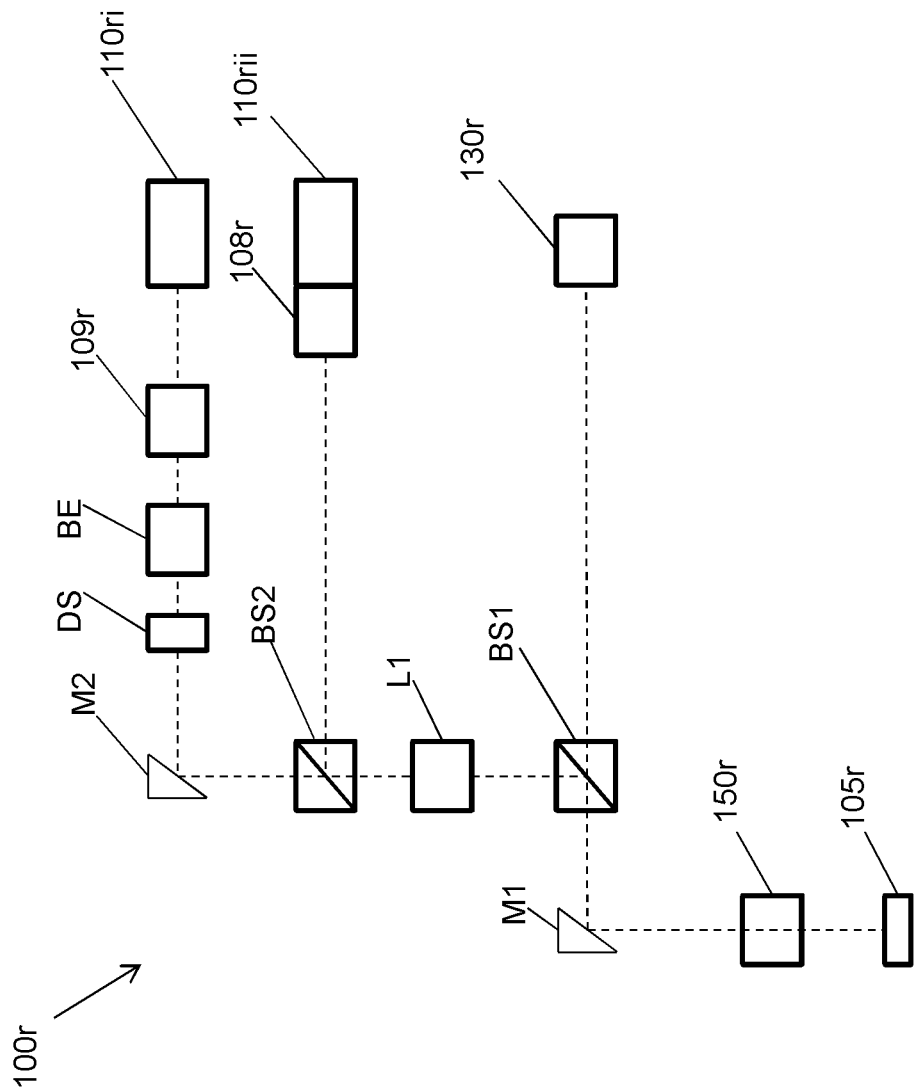
FIG. 8 shows an exemplary system according to at least one embodiment of the present disclosure utilizing a confocal laser apparatus and a bright field imaging apparatus.
Figure 9:
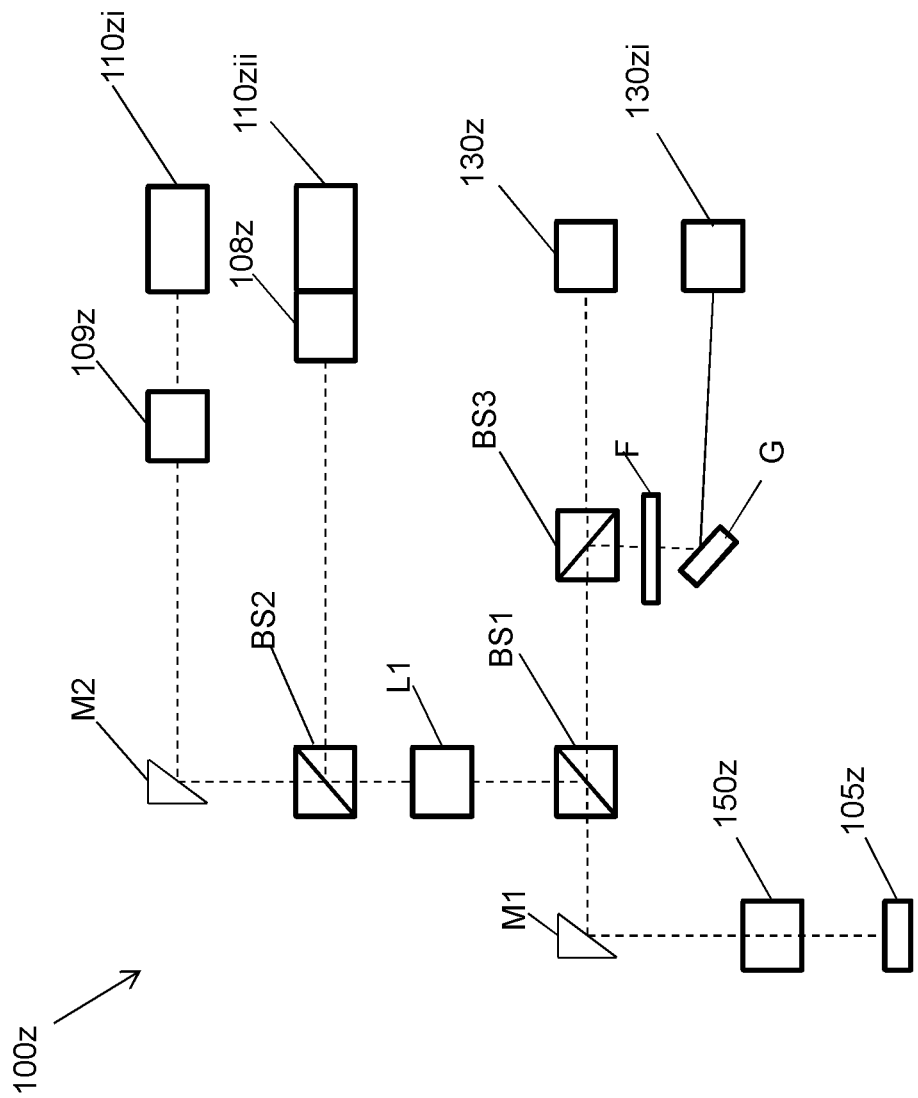
FIG. 9 shows an exemplary system of at least one embodiment of the present disclosure utilizing a Raman spectrometer apparatus.

While a particular arrangement of reflective devices and lenses is shown in FIG. 4a, various other arrangements may be provided to direct the radiation of the light sources onto the specimen as long as when the light sources are producing light radiation simultaneously or sequentially, light radiation from each of the light sources are substantially coincident on the specimen. For example, as shown in FIGS. 7-9 there may be more or less lenses, reflective devices, additional illumination sources, and/or other devices in the system. In particular, FIG. 7 shows an exemplary system 100b utilizing a bright field apparatus 110bi and a laser speckle apparatus 110bii for illumination of a stage 105b in an arrangement the same as to the system 105a in FIG. 4A but without lens L1. FIG. 8 shows a schematic of an exemplary system 100r utilizing a confocal laser apparatus and a bright field imaging apparatus, which includes one or more disks with spiral holes DS and a beam expander BE in the path of the light source 110ri. FIG. 9 shows a schematic of an exemplary system 100z utilizing a Raman spectrometer apparatus including a filter F, grating G, and second sensor 130zi for receiving light radiation from a grating G.

Figure 5A:
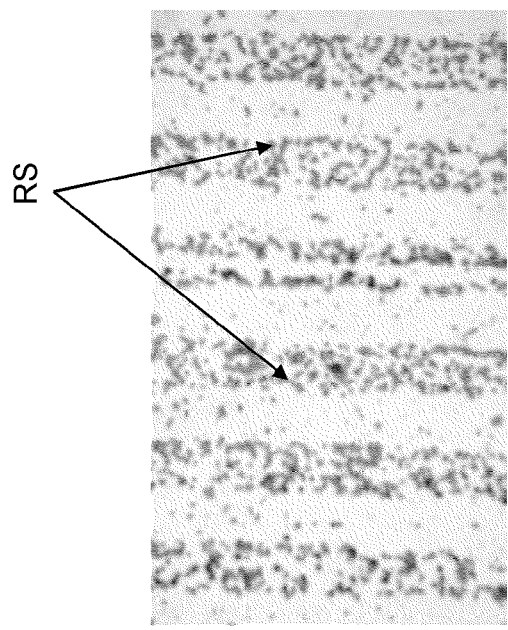
FIGS. 5a-5b depict bright field microscopic images of a sample target chip with 1) ideal (microfabricated) diffraction grating (FIGS. 5b), and 2) with the receptor sites having particles bound thereto (FIG. 5a).
Figure 5B:
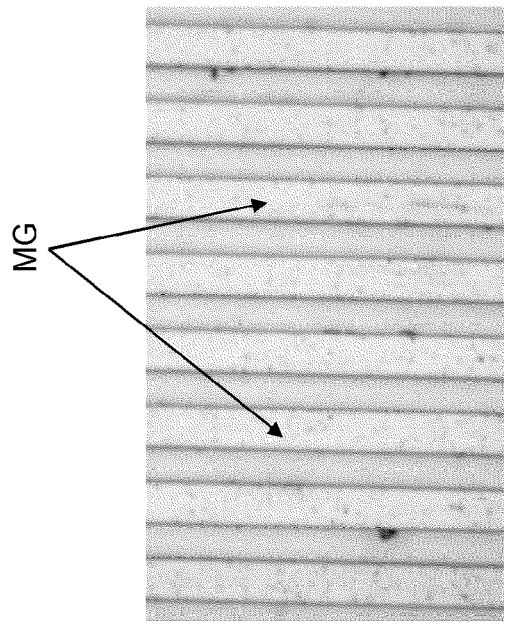

FIGS. 5a-5b show examples of bright field imaging results from a test chip. In particular, FIGS. 5a-5b show light radiation received by the sensor 130a and displayed on screen 102a of the PMMIS 100a. FIG. 5a shows receptor sites RS that are preprinted on the test chip using a micro-stamping process. After the micro-stamping process, anti-body coupled magnetic beads that have attracted certain target entities (such as proteins, peptides, small molecules, DNA, RNA, bacteria, cells and viruses) can be implemented on the test chip for a periodic arrangement. The magnetic beads selected for use are detectable through bright field detection and/or through laser diffractometry or other technique and can be analyzed and counted by an optional on-board counting algorithm programmed into an on-board computer of the device and studied. Strips of binder material may also be used on the test chip to selectively bind certain proteins. FIG. 5a depicts the particles in the receptor sites detected through bright field imaging. A broad range of biological entities may be detected using the system 100 of the present disclosure from small molecules to biomolecules (including proteins, DNA, and RNA) to bacteria, viruses, and cells by using the appropriate receptor combinations for the chip and the beads. FIG. 5b shows the micrograph of an example of a microfabricated diffraction grating structure.

Figure 6A:
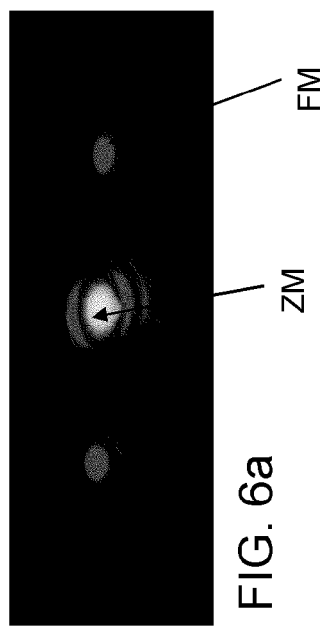
FIGS. 6a-6b depict views from sample target chips with diffractometric analysis with 1) laser illumination of diffraction grating of FIG. 5b (FIGS. 6b), and 2) with preprinted receptor sites with particles bound thereto (FIG. 6a).
Figure 6B:
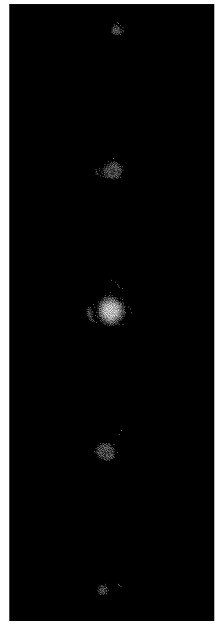

Referring to FIGS. 6a and 6b, optical modes produced by laser diffractometry (which can also be calculated by means of a Fourier analyses) are depicted using laser diffractometry. When a sample with a specific pattern is illuminated with a coherent light source (e.g., a laser), the light beams that reflect from the alternating lines with different phases (e.g, particle baring lines and empty lines in between; or the lines in a microfabricated grating that have different heights or refractive indices) interfere in a phase-sensitive manner forming a diffraction pattern with bright and dark spots called "modes". The intensities of the modes depend on the phase difference between the lines. Hence, the detection of mode intensities can reveal information about, height, refractive index of fabricated grating structure and/or the medium it is in; as well as quantity and various geometrical and optical properties of the particles that constitute the gratings. The diffraction pattern depends on the pattern of the grating itself. As shown in FIG. 5b, the microfabricated grating MG is represented as vertical columns. In the case of FIGS. 5a and 5b, since the periodicity of the samples are one dimensional, the resulting diffraction pattern is also one dimensional (all modes are in one line). It should be noted that the system 100 according to the present disclosure can capture and analyze diffraction patterns produced by other kinds of patterns having multiple dimensions.

FIG. 6a depicts the diffraction modes from the receptor sites having particles bound thereto. Depicted are the zero mode ZM and the first mode FM symmetric about the zero mode ZM. In FIG. 6b, these modes are visible even though they are dimmer as compared to the modes depicted in FIG. 6a.

While FIGS. 5a-5b and 6a-6b show the results of radiation collection for one technique, the system may be configured to collect radiation and display corresponding information regarding multiple techniques. For instance, while images from each source of light can be sequentially formed on the sensor, the system according to the present disclosure may be configured to simultaneously form the images on the sensor to provide an overlay of the images. This capability is particularly useful when there is a high temporal activity on the specimen, and images from various techniques each can provide data about the specimen, simultaneously and as a function of time.

As described above, the system 100 provides imaging and detection capabilities in a co-incident, co-located, and optionally simultaneous manner for a variety of applications. For example, a user can switch between one imaging technique (e.g., bright field illumination and capture) to another (e.g., laser diffractometry) without having to move the specimen horizontally out of position which enables diffractometric and bright field imaging of the same area on the specimen. The specimen may be moved vertically closer to or away from an objective lens for focusing or divergence of a reflected pattern as needed (without losing the microscopic field of view on the specimen.) One may also use multiple light sources and imaging techniques simultaneously including, but not limited to, bright field and laser speckle imaging. This capability eliminates the need to reposition and realign the specimen between multiple imaging systems, which can be cumbersome and introduce error. In the system 100 of the present disclosure, bright field imaging, laser diffractometry, and other techniques can be performed using the same microscopic objective and the same image sensor (CCD).

A combination or all of the following analysis techniques can be performed by the system: bright field imaging, darkfield imaging and surface plasmon resonance (by introducing illumination at an angle via a fiberoptic cable, with an occulting disk for dark field imaging), video imaging, localized surface plasmon resonance, interferometry, diffractometry (including binding of biological entities such as cells, viruses and biomolecules via affinity interactions with and without magnetic and nonmagnetic beads and spheres where such binding is random or guided by a pre-defined functional pattern), Michelson interferometry, speckle imaging, fluorescence imaging, spectroscopy, spectrophotometry, Raman spectroscopy, and confocal microscopy, among others. Each of the techniques used in the system 100 can reveal specific information about the specimen including, but not limited to, refractive index, molecular or material composition, physical and chemical properties, dimensions, phase, and color. The system 100 according to the present disclosure can obtain and provide information to the user from any combination of these techniques.

As discussed above, using the system 100, the analysis of a specific microscopic area on a specimen with multiple imaging techniques can be accomplished without the need for removing and re-aligning the specimen. The system 100 of the present disclosure, allows executing various interrogation and detection techniques sequentially or simultaneously, at the control of the user, or as controlled by an on-board computer. For example, a user may switch between one light source to another light source by pressing a button 106a or a button on a touch screen 102a. Such immediate control can allow the user to switch techniques quickly in order to observe specimen events as they are happening. The quantity, activity, and properties (including, but not limited to, dimensions, composition, refractive index, and patterns) of biological entities such as cells, viruses, biomolecules, small molecules, bacteria and spores can be detected and analyzed in an efficient and controlled manner. For example, the information can be location-tagged by introducing a GPS-enabled chip, shared wirelessly by introducing a wireless card or via a USB interface.

The system 100 according to the present disclosure may be particularly beneficial for imaging or detecting activities which may require multiple techniques (e.g., bright field and laser diffractometry). For example, the time period during which cell cycle activities or bacteria colonization occur may be short. Conventional imaging methods and apparatuses are not effective with regard to such activities and colonization because it takes too long to move and align the specimen from one system to another system and such motion and alignment introduces errors. By contrast, the system 100 of the present disclosure can effectively be used to provide multi-technique imaging in a short period of time. As described above, the system 100 may be operated in a simultaneous mode (i.e., light sources each providing light radiation at the same time) or in a switching sequence mode where the system 100 can be switched from one technique to another (e.g., turn on the laser and capture a diffraction image for a fraction of a second, turn laser off, turn white light on and capture image for a fraction of a second). Such a switching sequence may be controlled by the user or can be controlled by an on-board computer. Since the interrogation of the specimen is co-incident, images from the same location on the specimen can be generated using multiple techniques.

Figure 10:
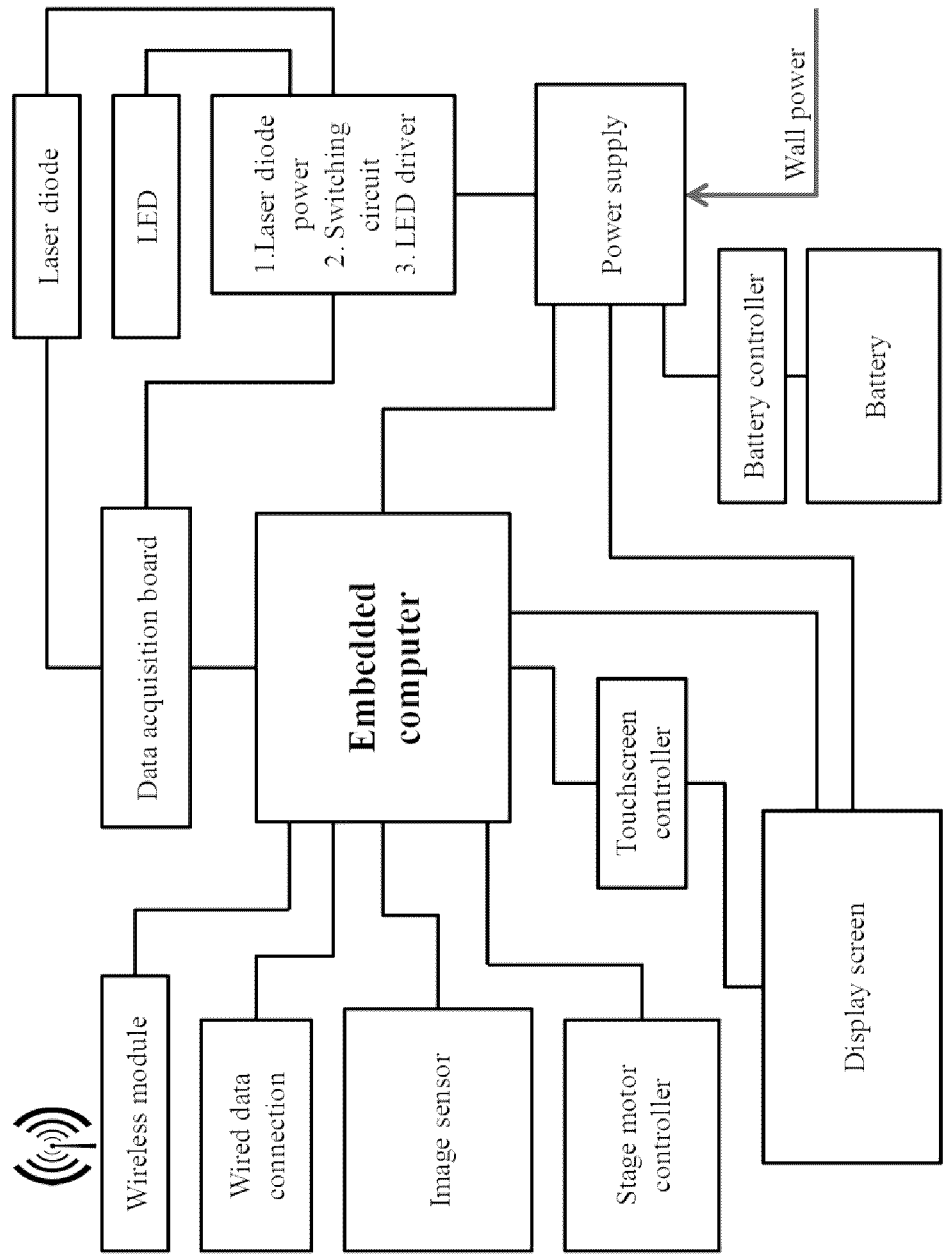
FIG. 10 shows a schematic layout of one embodiment of the control systems and electronics according to the present disclosure.

The communication and control circuits 108a may include a variety of devices for carrying out the control, analysis, process, and other functions of the system of the present disclosure. Such functions include data acquisition, processing, display, user interface, scanning stage control, wired and wireless communication, peripheral control and power management. A schematic layout of the electronics is shown in FIG. 10. As shown in FIG. 10, the power supply of the system may be powered by a battery and/or another power source (e.g., wall power), which then feeds the other components of the system, including the communication and control circuits 108a (e.g., embedded computer), screen, wireless components, illumination sources, sensor, and the like. The communication and control circuits 108a may include a low-power embedded on-board computer (e.g. igologic i2820) running an operating system (e.g. Windows XP) which provides graphical user interface (GUI) based control, data acquisition and processing. Data from an image sensor (e.g. DCU223C, Thorlabs, NJ, USA) may be transferred to the embedded on-board computer for processing. For data display and user interaction with the screen, a high resolution LCD display and a sunlight readable touchscreen (e.g. Panjit, AZ, USA) may be connected to the computer board. Various mechanisms may be provided for connection to external peripherals for data sharing (e.g. a USB connector) and wireless communication (e.g. a 802.11b/g embedded WiFi module, VNT6656, VIA, Taiwan or a GSM module) or cabled connection (e.g. local area network connection).

The system of the present disclosure may be powered in a variety of ways, such as by a high wattage ATX (Advanced Technology Extended) power supply (e.g. 120 W, PicoPSU, e-ITX, CA, USA) through a custom designed printed circuit board with compatible connectors as well as circuits and components for power on/off operation, regulation, relays, LED driver (e.g. 7021 BuckPlus, LEDdynamics, USA) as well as to power any additional component. An analog output of 0-1 V from the DAQ (Data Acquisition Board) may be included to control the power output from an LED while a potentiometer with a knob mounted on the display deck (104a) can be used for LED dimming control. The stage motor controller (e.g. TMCM-343, Trinamic Motion Control GmbH, Germany) may be connected to the on-board embedded computer via serial interface and to the motors of the stage (105a) via an interface board.

Figure 11:
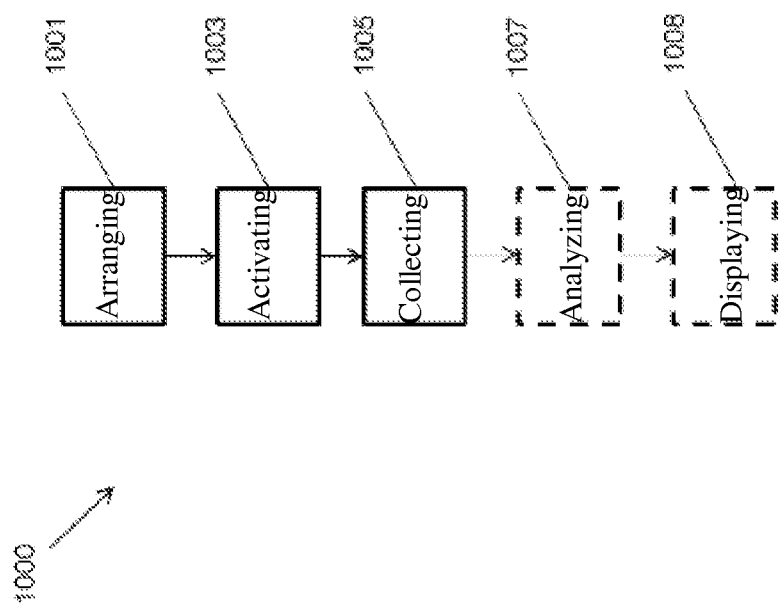
FIG. 11 shows a flowchart of a method of performing multi-technique imaging according to at least one embodiment of the present disclosure.

FIG. 11 shows a flowchart of a method for performing multi-technique imaging 1000. As shown in FIG. 11, the method 1000 includes the step 1001 of arranging a plurality of reflective devices to direct at least part of light radiation from each of at least two illumination sources in the direction of a surface supporting a specimen such that the at least part of the light radiation from each of the at least two illumination sources are substantially coincident on the specimen. The method 1000 also includes the step 1003 of activating the at least two illumination sources to produce light radiation. The method 1000 further includes the step 1005 of collecting the light radiation from the at least two illumination sources reflected or transmitted by the specimen. As shown in FIG. 11, the method 1000 optionally includes the step 1007 of analyzing at least a portion of the collected light radiation and the step 1008 of displaying at least a portion of the collected light radiation and/or the results of the analysis of the collected light radiation.

Those skilled in the art will recognize that numerous modifications can be made to the specific implementations described above. Therefore, the subject matter of this disclosure is not to be limited to the specific embodiments illustrated and described above. The systems and methods described above may be amended to encompass variations, alternatives, modifications, improvements, equivalents, and substantial equivalents of the embodiments and teachings disclosed herein, including those that are presently unforeseen or unappreciated, and that, for example, may arise from applicants/patentees and others.

That which is claimed is:

1. A selective system for bright field imaging technique and diffraction imaging measurement technique, comprising:
   a surface for supporting a specimen, the surface configured to be moved laterally and vertically;
   a first illumination source for the bright field imaging technique and a second illumination source for the diffraction measurement imaging technique;
   a plurality of reflective and refractive devices arranged to direct and focus at least part of the light radiation from each of the first and second illumination sources to the surface such that the at least part of the light radiation from each of the first and second illumination sources illuminates substantially the same area on the surface;
   a sensor configured to receive light radiation from the specimen; and
   a power interface configured to power the first and second illumination sources and the sensor,
   wherein vertical movement of the surface from a first position to a second position allows the system to selectively change between i) the bright field imaging technique to ii) the diffraction measurement imaging technique without the need to i) move the surface laterally, ii) move the sensor, or iii) move any of the plurality of reflective and refractive devices.

2. The system of claim 1, further comprising a display for presenting at least information based on the light radiation received by the sensor.

3. The system of claim 1, further comprising a manipulator controlled by an on-board computer configured to move and adjust the surface either by user inputs or automatically.

4. The system of claim 1, wherein at least one of the first and second illumination sources is at least one of a non-white light source, a white light source, and a laser source.

5. The system of claim 1, wherein the sensor is at least one of a charge coupled device, a photodiode, and a digital imaging sensor.

6. The system of claim 5, further comprising a processor system configured to analyze the light radiation received by the sensor.

7. The system of claim 6, further comprising a wireless communication module including an antenna for transferring information from the processor.

8. The system of claim 1, wherein the system is portable.

9. The system of claim 1, wherein the power interface includes a battery.

10. The system of claim 1, further comprising:
a common objective lens arrangement disposed proximate to the surface and utilized in both the bright field imaging technique and the diffraction measurement imaging technique.

11. The system of claim 1, further comprising:
a global positioning sensor (GPS)-enabled chip configured to provide location information of the system.

12. A method of selectively performing bright field imaging measurement technique and diffraction imaging measurement technique, the method comprising:
arranging a plurality of reflective and refractive devices to direct at least part of light radiation from each of a first illumination source associated with the bright field imaging measurement technique and a second illumination source associated with the diffraction imaging measurement technique in the direction of a surface supporting a specimen such that the at least part of the light radiation from each of the first and second illumination sources illuminates substantially the same area on the surface;
activating the first and second illumination sources to produce light radiation;
collecting the light radiation from the first and second illumination sources reflected or transmitted by the specimen; and
moving the surface vertically from a first position to a second position to thereby allow the system to selectively change between i) the bright field imaging technique to ii) the diffraction measurement imaging technique without the need to i) move the surface laterally, or ii) move any of the plurality of reflective and refractive devices.

13. The method of claim 12, further comprising displaying at least a portion of the collected light radiation.

14. The method of claim 12, further comprising analyzing the collected light radiation.

15. The method of claim 12, further comprising:
controlling a manipulator by an on-board computer configured to move and adjust the surface either by user inputs or automatically.

16. The method of claim 12, wherein at least one of the first and second illumination sources is at least one of a non-white light source, a white light source, and a laser source.

17. The method of claim 12, further comprising:
sensing light radiation from the specimen by a sensor.

18. The method of claim 17, further comprising:
processing and analyze data associated with the light radiation received by the sensor by a processor.

19. The method of claim 18, further comprising communicating information from the processor.

20. The method of claim 12, wherein the first and second illumination sources are powered by a power interface including a battery.

* * * * *